(12) United States Patent
Stark et al.

(10) Patent No.: US 8,968,807 B1
(45) Date of Patent: Mar. 3, 2015

(54) USE OF ETHYLENE DIAMINE METAL COMPLEXES TO DELIVER HIGHLY ABSORBABLE METALS FOR ANIMAL NUTRITION

(71) Applicant: Zinpro Corporation, Eden Prairie, MN (US)

(72) Inventors: Peter A. Stark, Inver Grove Heights, MN (US); Cory Shawn Kending, Champlin, MN (US)

(73) Assignee: Zinpro Corporation, Eden Prairie, MN (US)

( * ) Notice: Subject to any disclaimer, the term of this patent is extended or adjusted under 35 U.S.C. 154(b) by 0 days.

(21) Appl. No.: 14/034,851

(22) Filed: Sep. 24, 2013

(51) Int. Cl.
*A23L 1/304* (2006.01)
*A23K 1/175* (2006.01)

(52) U.S. Cl.
CPC .................................... *A23K 1/175* (2013.01)
USPC ................ 426/74; 426/2; 426/615; 426/630; 426/648

(58) Field of Classification Search
USPC ................................ 426/74, 2, 615, 648, 630
See application file for complete search history.

(56) References Cited

U.S. PATENT DOCUMENTS

| | | | |
|---|---|---|---|
| 3,131,048 A * | 4/1964 | Balassa | 71/1 |
| 5,698,724 A | 12/1997 | Anderson et al. | |
| 6,265,438 B1 | 7/2001 | Steward | |
| 2010/0284994 A1 | 11/2010 | Hutas | |
| 2012/0160001 A1 | 6/2012 | Ponder et al. | |
| 2012/0231112 A1* | 9/2012 | Wreesmann et al. | 426/2 |

* cited by examiner

*Primary Examiner* — Helen F Heggestad
(74) *Attorney, Agent, or Firm* — McKee, Voorhees & Sease

(57) ABSTRACT

Use of ethylene diamine metal complexes, preferably of copper, zinc, iron and manganese in highly absorbable formats for animal nutrition.

5 Claims, 3 Drawing Sheets

Caco-2 cell permeability

US 8,968,807 B1

USE OF ETHYLENE DIAMINE METAL COMPLEXES TO DELIVER HIGHLY ABSORBABLE METALS FOR ANIMAL NUTRITION

FIELD OF THE INVENTION

The field of the invention is animal nutritional supplementation of trace minerals in a highly bioavailable, absorbable format.

BACKGROUND OF THE INVENTION

The presence of essential metals sometimes referred to as trace minerals, in sufficient quantities and in a biologically available form in diet is necessary for maintaining the health and well-being of domestic animals and poultry. Because essential metals such as copper, iron, manganese and zinc are often deficient in common feed ingredients, supplemental amounts of these nutrients are often added to the feed of domesticated animals and poultry. Many commercial feed additives have been developed to provide the essential metals in forms that are readily biologically utilizable. The degree of biological availability of nutrients is often referred to as "bioavailability". Bioavailability of essential metals depends on the physical and/or chemical properties of the form in which the metal is present in the diet. Increased bioavailability of supplemental metals is beneficial because it allows the use of lower concentrations of the metals in the diet to meet the nutritional needs of animals, while lowering the potential harmful effects of high levels of these metals both on the animals and on the environment.

Several commercial products are available in which trace elements are more bioavailable than the corresponding inorganic source of the metal. The enhanced bioavailability is attributed to the association of the metal with an organic molecule, generally known as a ligand. This association or bonding results in the increased availability of the metal for utilization by animals, i.e. increased bioavailability. The increased bioavailability of the essential elements in these products is the result of increased solubility, greater stability in the gut, enhanced absorption into circulation and/or improved metabolic utilization.

Different types of products that contain a trace element associated with an organic ligand are commercially available. These can be classified in different groups based on the nature of the ligand used in manufacturing the product. In one class of products, amino acids are used as the ligands that form complexes or chelates with the metal. Examples of these products are described in U.S. Pat. Nos. 3,941,818; 3,950,372; 4,067,994; 4,863,898 4,900,561; 4,948,594; 4,956,188; 5,061,815; 5,278,329; 5,583,243; and 6,166,071. A second group of feed additives include the metal salts of short chain carboxylic acids such as propionic acid (See U.S. Pat. Nos. 5,591,878, 5,707,679, 5,795,615 and 5,846,581). A third group of trace element additives is classified by the American Feed Control Officials as Metal Proteinate and defined as "the product resulting from the chelation of a soluble salt with amino acids and/or partially hydrolyzed protein". Examples of these products are described in U.S. Pat. Nos. 3,440,054, 3,463,858, 3,775,132, 3,969,540, 4,020,158, 4,076,803, 4,103,003, 4,172,072 and 5,698,724.

The common assignee of the present application has in the past synthesized and patented metal complexes of amino acids as a more bioavailable source of the essential elements. The following are examples of these patents: U.S. Pat. Nos. 3,941,818; 3,950,372; 4,021,569; 4,039,681; and 4,067,994 disclose 1:1 complexes of alpha amino acids, preferably DL-methionine with the transition metals zinc, chromium, manganese and iron. The formation of similar complexes with L-methionine is disclosed in U.S. Pat. No. 5,278,329. U.S. Pat. Nos. 4,900,561 and 4,948,594 disclose copper complexes of alpha amino acids containing terminal amino groups. Complexes of copper, manganese, zinc and iron with alpha hydroxyl aliphatic carboxylic acids are disclosed in U.S. Pat. Nos. 4,956,188 and 5,583,243. U.S. Pat. Nos. 4,670,269 and 4,678,854 disclose complexes of cobalt with polyhydroxy carboxylic acid such as glucoheptanoic acid. Complexes of the amino acid L-lysine with trace elements are disclosed in U.S. Pat. No. 5,061,815. The effectiveness of the compounds disclosed in these patents has been demonstrated from data provided in some of these patents and in numerous scientific publications and technical reports.

The above patents describe the use of pure synthetic or natural amino acids. In U.S. Pat. No. 5,698,724 the assignee of the current application disclosed the synthesis of complexes of essential elements with natural amino acids obtained by the hydrolysis of proteins. Since this patent was issued, a large number of field studies have demonstrated that metals from these complexes are more bioavailable than metals from inorganic sources.

Ethylene diamine (EDA) is well known in the chemistry arena and is a building block for many compounds and polymers. It is also an important ligand for metal complexation. As such, it has been chemically modified to produce one of the best and well known chelating agents, EDTA (ethylenediame tetracetic acid). Finding a good ligand for chemical complexation of metals is completely different than finding a good ligand for nutritional delivery of the metal to animals for animal performance. There are many factors that determine if a ligand will be effective for delivery of a mineral to an animal. Often it can be difficult to evaluate the effectiveness of a given metal ligand since inorganic mineral is a nutritionally viable source of mineral. Many factors determine if organic metal sources are suitable to provide a bioavailable source of trace minerals. A good carrier for the trace mineral must be an organic molecule which provides solubility at physiological conditions, stability in stomach acid; it must be able to be absorbed intact through the intestinal wall, and it must release the trace mineral to the animal body for use, rather than excrete it.

The increased performance or efficacy of an organic trace mineral must be determined by careful selection of the study so as to be sure you are identifying a performance response versus a mineral response. Comparison of the same metal levels versus an inorganic control is typically required. Absorption of the metal-ligand complex intact is required to be considered an organic trace mineral. If disassociation occurs before absorption one would not expect performance differences from inorganic minerals.

With all this in mind an effective organic trace mineral must be soluble and stable at physiological conditions and the mineral must be absorbed intact. Common ligands that have been used in the area of animal nutrition are propionic acid, amino acids, hydroxy acids, proteinates, etc.

Accordingly, it is a primary objective of the present invention to provide a preferred small molecule ligand of the metals copper, iron, zinc and manganese in a format which is highly absorbable, soluble at physiological conditions, stable in stomach acid, absorbed intact and able to release the mineral to the animal rather than excrete it.

Another objective of the present invention is to provide the above metal ligands in an easily processable form, and one that is easy to make, and easy to use for supplementation.

The method and manner of accomplishing the above objectives as well as others will become apparent from the detailed description of the invention.

SUMMARY OF THE INVENTION

Use of ethylene diamine metal complexes, preferably of copper, zinc, iron and manganese in highly absorbable formats for animal nutrition.

DETAILED DESCRIPTION OF THE PREFERRED EMBODIMENTS

Figure 1:
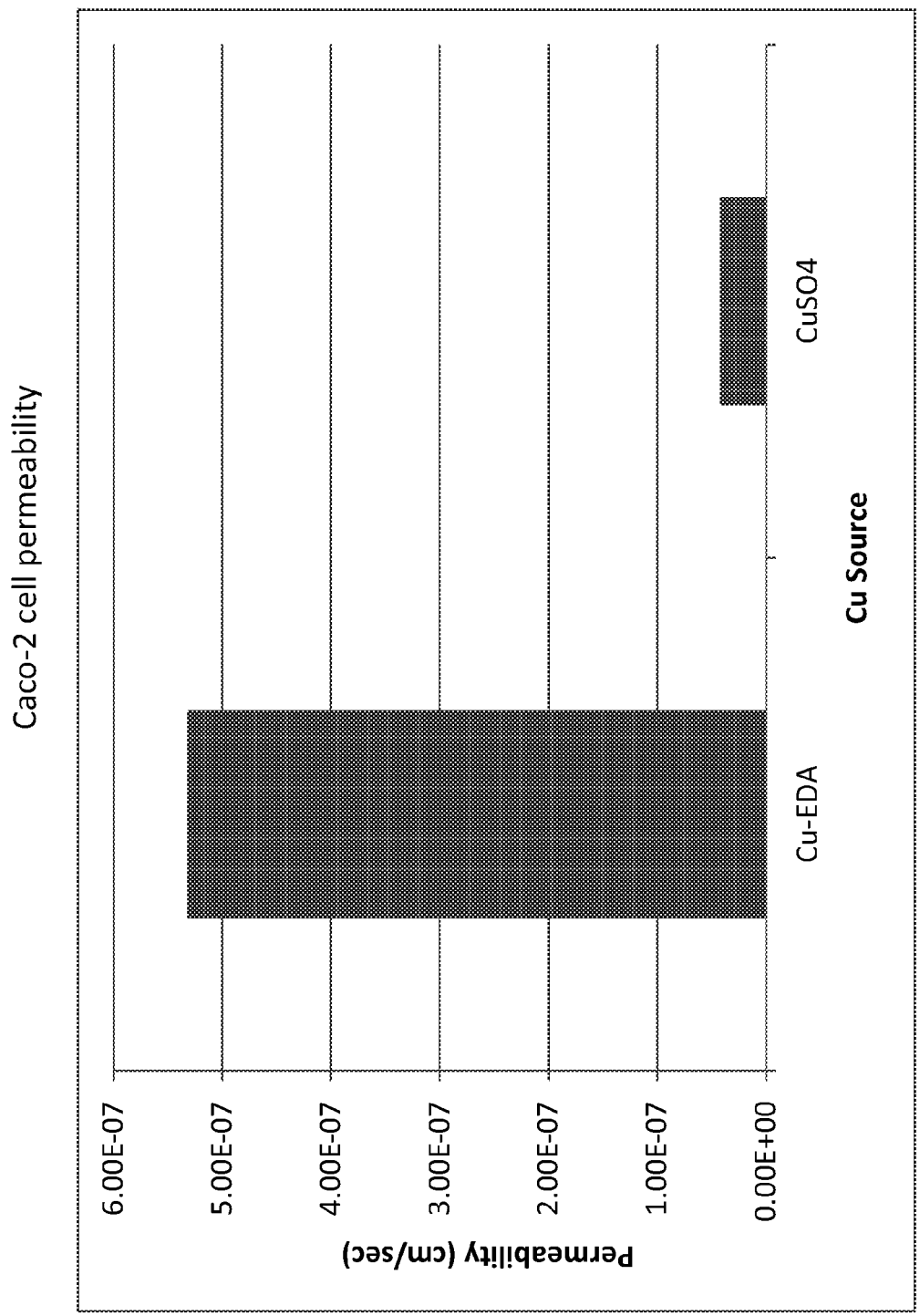
FIG. 1 shows a graph of cell permeability for Cu-EDA.

It is important to note that the organic moiety of the ligand of this invention is ethylene diamine alone, not ethylene diamine tetraacetic acid (EDTA) or other larger molecules. This is important as the smaller molecule means less bulk and increases the chances of a high rate of successful absorption through the intestine and assimilation into the animal's bio system, rather than simply passing through the system as excrement. Of course, if it does the latter, it is simply wasted without any nutritional benefit to the animal.

As far as the inventor knows, EDA has not been utilized as a delivery ligand for metals even though it is well known as a metal complexing agent. It has several advantages over some of the previously listed prior art organic metal ligands. It is small which allows for higher metal concentrations over some of the other ligands. It is a stable complex whereas some of the other organic ligands form too weak of a complex such as hydroxyl acids and straight acids. Ethylene diamine overcomes these problems. It is difficult to predict what will be an effective organic trace mineral. It is easy to know what would not work due to solubility and stability issues but whether or not a complex can be absorbed must be determined through experiments. Due to its small size, solubility and absorption it meets all requirements for an effective organic trace mineral complex. The general structure of these complexes is as follows:

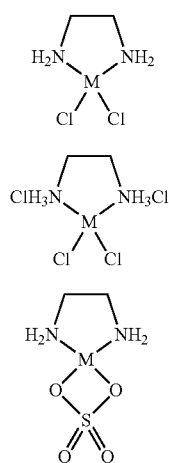

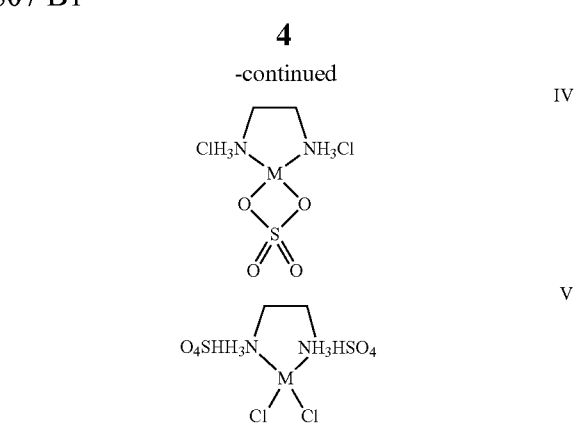

The counter ion will vary depending on what metal material was used for the formation. For example, $ZnCl_2$ will have the chloride counter ions and $ZnSO_4$ will have the sulphate. Preferred metals are Zn, Fe, Mn, Cu. Depending on the synthetic conditions the complex can be made from the free amine as well as the protonated amine. These structures show the protonated amine (II, IV, and V) which will also work. The counterion can be any anion used to balance the charges and provide a neutral ligand. However, the most likely and preferred are the chloride or the bisulfate anion (on the amine like structure V). The phrase "counter ion" as used here refers to both the counter ion for the metal and the counter ion for the nitrogen if it is protonated.

The products may be used in the carrier-free form or with a non-toxic carrier. Suitable carriers include: calcium hydrogen phosphate, calcium carbonate, silica, ground corn cobs, whey, cellulose and other wood fibers and powdered sugar or a mixture of any of the above.

In the following examples the preparation and nutritional supplementation use, are demonstrated for zinc, copper, iron and manganese EDA ligands, and they are compared with inorganic sources to demonstrate bioavailability for small molecules.

The examples are to be taken as illustrative and non-limiting. While applicant has only used EDA with the four metals here mentioned, others may be able to be made and used as well, such as chromium, etc.

EXAMPLES

Example 1

Zinc EDA Chloride 1,2 Diaminoethane dihydrochloride—zinc(II) chloride

EDA (100 ml, 1.5 mols) was dissolved in 1 L of dI water and heated to 50° C. To this solution was added conc. Hydrochloric Acid (437.5 mL, 5.25 mols) and the solution was allowed to stir for 15 minutes. Zinc oxide (50.3 g, 1.5 mols) was added in one portion and stirred for 45 minutes or until the suspension became a solution. Upon completion the reaction was dried within a vacuum oven to a white solid (314 g).

ICP: 27% Zn $^1$H NMR ($D_2O$, 300 MHz) δ 3.23 (broad s, 4H)

IR (KBr): 1598, 1574, 1493, 1444 $cm^{-1}$

Anal. Found: C, 9.79; H, 3.73; N, 11.13; Cl, 51.24.

Example 2

Zinc EDA Chloride 1,2 Diaminoethane dihydrochloride—zinc(II) chloride

EDA Dihydrochloride (22 g, 0.16 mols) was dissolved in 200 mL of dI water and heated to 40° C. To this solution was added zinc chloride (23.6 mL, 0.16 mols) that had been dissolved in a separate vessel. This solution was heated for two hours at 40° C. with continuous stirring. Upon completion the reaction was dried within a vacuum oven to a white solid (34 g).

ICP: 26% Zn
$^1$H NMR ($D_2O$, 300 MHz) δ 3.40 (broad s, 4H)
IR (KBr): 1581, 1486, 1465 $cm^{-1}$
Anal. Found: C, 8.97; H, 3.55; N, 10.21; Cl, 52.36.

Example 3

Zinc EDA Sulfate 1,2 Diaminoethane hydrosulfuric—zinc(II) sulfate

EDA (33 ml, 0.5 mols) was dissolved in 250 mL of dI water and heated to 50° C. $ZnSO_4$ Heptahydrate (143 g, 0.5 mols) was suspended in 50 mL of dI water in a separate vessel and stirred for 5 minutes with a magnetic stir bar. The suspension was added in one portion to the reaction vessel. The suspension was clarified with the addition of conc. $H_2SO_4$ (36N, 28 mL). The solution was then heated for 1.5 hours at 50° C. and then evaporated within a vacuum oven to a white solid (127 g).

ICP: 20.9% Zn
$^1$H NMR ($D_2O$, 300 MHz) δ 3.39 (s, 4H)
IR (KBr): 1595, 1573, 1490, 1473 $cm^{-1}$
Anal. Found: C, 7.55; H, 3.07; N, 8.64; S, 19.37.

Example 4

Copper EDA Chloride 1,2 Diaminoethane dihydrochloride—copper(II) chloride

EDA (33 ml, 0.5 mols) was dissolved in 250 mL of dI water and heated to 50° C. Copper Chloride dihydrate (85.24 g, 0.5 mols) was suspended in 50 mL of dI water in a separate vessel and stirred for 5 minutes with a magnetic stir bar. The suspension was added in one portion to the reaction vessel. The suspension was clarified with the addition of conc. HCl (12M, 83 mL). The solution was then heated for 1.5 hours at 50° C. and then evaporated within a vacuum oven to a green blue solid (100 g).

ICP: 21.4% Cu
$^1$H NMR ($D_2O$, 300 MHz) δ 3.24 (broad s, 4H)
IR (KBr): 1573, 1493 $cm^{-1}$
Anal. Found: C, 10.42; H, 3.89; N, 11.76; Cl, 53.40.

Example 5

Copper EDA Chloride 1,2 Diaminoethane dihydrochloride—copper(II) chloride

EDA Dihydrochloride (100 g, 0.76 mols) was dissolved in 600 mL of dI water and heated to 40° C. To this solution was added copper chloride (100.76 g, 0.76 mols) that had been dissolved in a separate vessel. This solution was heated for two hours at 60° C. with continuous stirring. Upon completion the reaction was dried within a vacuum oven to a white solid (178 g).

ICP: 23.54% Cu
$^1$H NMR ($D_2O$, 300 MHz) δ 3.17 (s, 4H)
IR (KBr): 1576, 1502 $cm^{-1}$
Anal. Found: C, 9.12; H, 3.77; N, 10.36; Cl, 52.73.

Example 6

Copper EDA Chloride—CuO 1,2 Diaminoethane dihydrochloride—copper(II) chloride EDA (33 ml, 0.5 mols) was dissolved in 250 mL of dI water and heated to 50° C. Copper oxide (39.8 g, 0.5 mols) was added in one portion to the reaction vessel. The suspension was clarified with the addition of conc. HCl (12M, 166 mL). The solution was then heated for 2.5 hours at 50° C. and then evaporated within a vacuum oven to a light yellow solid (143 g).

ICP: 23.68% Cu
IR (KBr): 1571, 1495 $cm^{-1}$
Anal. Found: C, 8.16; H, 3.53; N, 9.18; Cl, 51.73.

Example 7

Copper EDA Sulfate 1,2 Diaminoethane dihydrogen sulfate—copper(II) sulfate

EDA (33 ml, 0.5 mols) was dissolved in 250 mL of dI water and heated to 50° C. Copper Sulfate Pentahydrate (124.9 g, 0.5 mols) was suspended in 50 mL of dI water in a separate vessel and stirred for 5 minutes with a magnetic stir bar. The suspension was added in one portion to the reaction vessel. The suspension was clarified with the addition of conc. $H_2SO_4$ (36N, 28 mL). The solution was then heated for 1.5 hours at 50° C. and then evaporated within a vacuum oven to a blue solid (180 g).

ICP: 17.9% Cu
$^1$H NMR ($D_2O$, 300 MHz) δ 3.22 (broad s, 4H)
IR (KBr): 1616, 1545, 1507, 1486 $cm^{-1}$
Anal. Found: C, 6.09; H, 4.22; N, 6.81; S, 15.89.

Example 8

Iron EDA Sulfate 1,2 Diaminoethane dihydrogen sulfate—iron(II) sulfate

EDA (33 ml, 0.5 mols) was dissolved in 250 mL of dI water and heated to 50° C. $FeSO_4$ Heptahydrate (139.01 g, 0.5 mols) was suspended in 50 mL of dI water in a separate vessel and stirred for 5 minutes with a magnetic stir bar. The suspension was added in one portion to the reaction vessel. The suspension was clarified with the addition of conc. $H_2SO_4$ (36N, 28 mL). The solution was then heated for 1.5 hours at 50° C. and then evaporated within a vacuum oven to a light green solid (153.74 g).

ICP: 16.1% Fe
IR (KBr): 1611, 1530, 1509 $cm^{-1}$
Anal. Found: C, 6.45; H, 3.50; N, 7.24; S, 20.09.

Example 9

Iron EDA Chloride 1,2 Diaminoethane dihydrochloride—iron(II) chloride

EDA (33 ml, 0.5 mols) was dissolved in 250 mL of dI water and heated to 50° C. Ferrous Chloride tetrahydrate (99.4 g, 0.5 mols) was suspended in 50 mL of dI water in a separate vessel and stirred for 5 minutes with a magnetic stir bar. The suspension was added in one portion to the reaction vessel. The suspension was clarified with the addition of conc. HCl (12M, 83 mL). The solution was then heated for 1.5 hours at 50° C. and then evaporated within a vacuum oven to a light green solid (111 g).

ICP: 22.7% Fe
IR (KBr): 1617, 1509 $cm^{-1}$
Anal. Found: C, 8.72; H, 3.62; N, 9.88; Cl, 50.44.

Example 10

Manganese EDA Chloride 1,2 Diaminoethane dihydrochloride—manganese(II) chloride

EDA (33 ml, 0.5 mols) was dissolved in 250 mL of dI water and heated to 50° C. Manganese Chloride tetrahydrate (99 g, 0.5 mols) was suspended in 50 mL of dI water in a separate vessel and stirred for 5 minutes with a magnetic stir bar. The suspension was added in one portion to the reaction vessel. The suspension was clarified with the addition of conc. HCl (12M, 83 mL). The solution was then heated for 1.5 hours at 50° C. and then evaporated within a vacuum oven to a light pink solid (119 g).

ICP: 21.7% Mn
IR (KBr): 1620, 1616, 1511, 1505 $cm^{-1}$
Anal. Found: C, 9.12; H, 3.85; N, 10.42; Cl, 53.65.

Example 11

Manganese EDA Chloride—MnO 1,2 Diaminoethane dihydrochloride—manganese(II) chloride EDA (33 ml, 0.5 mols) was dissolved in 250 mL of dI water and heated to 50° C. Manganese oxide (43.5 g, 0.5 mols) was added in one portion to the reaction vessel. The suspension was clarified with the addition of conc. HCl (12M, 166 mL). The solution was then heated for 2.5 hours at 50° C. and then evaporated within a vacuum oven to a light pink solid (131 g).

ICP: 25.08% Mn
IR (KBr): 1617, 1590, 1509 $cm^{-1}$
Anal. Found: C, 8.57; H, 3.61; N, 9.57; Cl, 48.51.

Example 12

Manganese EDA Sulfate 1,2 Diaminoethane dihydrogen sulfate—manganese(II) sulfate EDA (33 ml, 0.5 mols) was dissolved in 250 mL of dI water and heated to 50° C. $MnSO_4$ monohydrate (84.5 g, 0.5 mols) was suspended in 50 mL of dI water in a separate vessel and stirred for 5 minutes with a magnetic stir bar. The suspension was added in one portion to the reaction vessel. The suspension was clarified with the addition of conc. $H_2SO_4$ (36N, 28 mL). The solution was then heated for 1.5 hours at 50° C. and then evaporated within a vacuum oven to a light pink solid (146 g).

ICP: 16.5% Mn
IR (KBr): 1675, 1638, 1609, 1532 $cm^{-1}$
Anal. Found: C, 7.09; H, 3.30; N, 8.10; S, 19.78.

Example 13

Zinc EDA Chloride—(MeOH)

1,2 Diaminoethane—zinc(II) chloride

Zinc (II) Chloride (102 g, 0.75 mols) was dissolved in 800 mL of 60° C. methanol to form a clear solution. Ethylenediamine (50 mL, 0.75 mols) was added slowly due to the extreme exothermic nature of the reaction. A light white solid immediately precipitated from the solution and this suspension was stirred for an additional hour. The white solid (115 g) was filtered and dried in a vacuum oven.

$^1$H NMR ($D_2O$, 300 MHz) δ 3.01 (d, 4H)
IR (KBr): 1573 $cm^{-1}$
ICP: 32.7% Zn
Anal. Found: C, 12.34; H, 4.19; N, 14.2; Cl 35.83

Example 14

Copper EDA Chloride—(MeOH)

1,2 Diaminoethane—copper(II) chloride

Copper (II) Chloride dihydrate (56 g, 0.33 mols) was dissolved in 500 mL of 60° C. methanol to form an emerald green solution. Ethylenediamine (22 mL, 0.33 mols) was added slowly due to the exothermic nature of the reaction. A light blue solid immediately precipitated from the solution and this suspension was stirred for an additional hour. The light blue solid (61 g) was filtered and dried in a vacuum oven.

$^1$H NMR ($D_2O$, 300 MHz) δ 3.16 (s, 4H)
IR (KBr): 1570 $cm^{-1}$
ICP: 33.4% Cu
Anal. Found: C, 12.44; H, 4.13; N, 14.14; Cl 36.16

Example 15

Manganese EDA Chloride—(MeOH)

1,2 Diaminoethane—manganese(II) chloride

Manganese (II) Chloride (55 g, 0.44 mols) was dissolved in 500 mL of 60° C. methanol to form a light brown solution.

Ethylenediamine (29.4 mL, 0.44 mols) was added slowly due to the exothermic nature of the reaction. A light tan solid immediately precipitated from the solution and this suspension was stirred for an additional hour. The light tan solid (67 g) was filtered and dried in a vacuum oven prior to analysis.
IR (KBr): 1591, 1510 cm$^{-1}$
ICP: 22% Mn
Anal. Found: C, 15.08; H, 4.84; N, 13.28; Cl 30.77

Example 16

Iron EDA Chloride—(MeOH)

1,2 Diaminoethane—iron(II) chloride (20788-115)—MeOH

Ferrous (II) Chloride Tetrahydrate (50 g, 0.25 mols) was dissolved in 500 mL of 60° C. methanol to form a dark green solution. Ethylenediamine (16.8 mL, 0.25 mols) was added slowly due to the exothermic nature of the reaction. A dark green solid immediately precipitated from the solution and this suspension was stirred for an additional hour. The dark green solid became a dark red solid (38 g) upon filtering and drying in a vacuum oven.
$^1$H NMR (D$_2$O, 300 MHz) δ 3.17 (broad s, 4H)
IR (KBr): 1510 cm$^{-1}$
ICP: 26.5% Fe
Anal. Found: C, 12.16; H, 5.03; N, 10.89; Cl 32.31

Example 17

Zinc EDA-Chloride Sulfate 1,2 Diaminoethane dihydrochloride-zinc(II) sulfate

EDA Hydrochloride (22 g, 0.16 mols) was dissolved in 100 mL of dI water and heated to 50° C. To this solution was added Zinc Sulfate heptahydrate (50.3 g, 0.17 mols). The solution was stirred at 50° C. for an additional 2 hours. Upon completion the reaction was dried in a vacuum oven to a white solid (58 g).
ICP: 22.5% Zn
IR (KBr): 1595, 1574, 1491, 1474 cm$^{-1}$ Example 18

The Cu$^{2+}$ was transported in (HBSS) Hanks Buffered Salt Solution from pH 5.5 to 7.4 at 37° C. The concentration was 100 μg/mL of Cu$^{2+}$. Each data point is the average of three determinations. The Caco-2 (heterogeneous human epithelial colorectal adenocarcinoma) cell culture model was used, which is recognized by FDA to characterize drug absorption pattern. The testing solution with appropriate concentrations of product was loaded onto the apical (donor) side. A donor samples (2500 μL) and a receiver sample were taken at 0, 3, and 6 h followed by the addition of 2500 μL of fresh donor solution to the donor side or 2500 μL of fresh buffer to the receiver side. Metal content was measured by ICP-OES.
FIG. 1 shows the results graphically and demonstrates the clear superiority of Cu-EDA over the CuSO$_4$.

Example 19

Sheep

Figure 2:
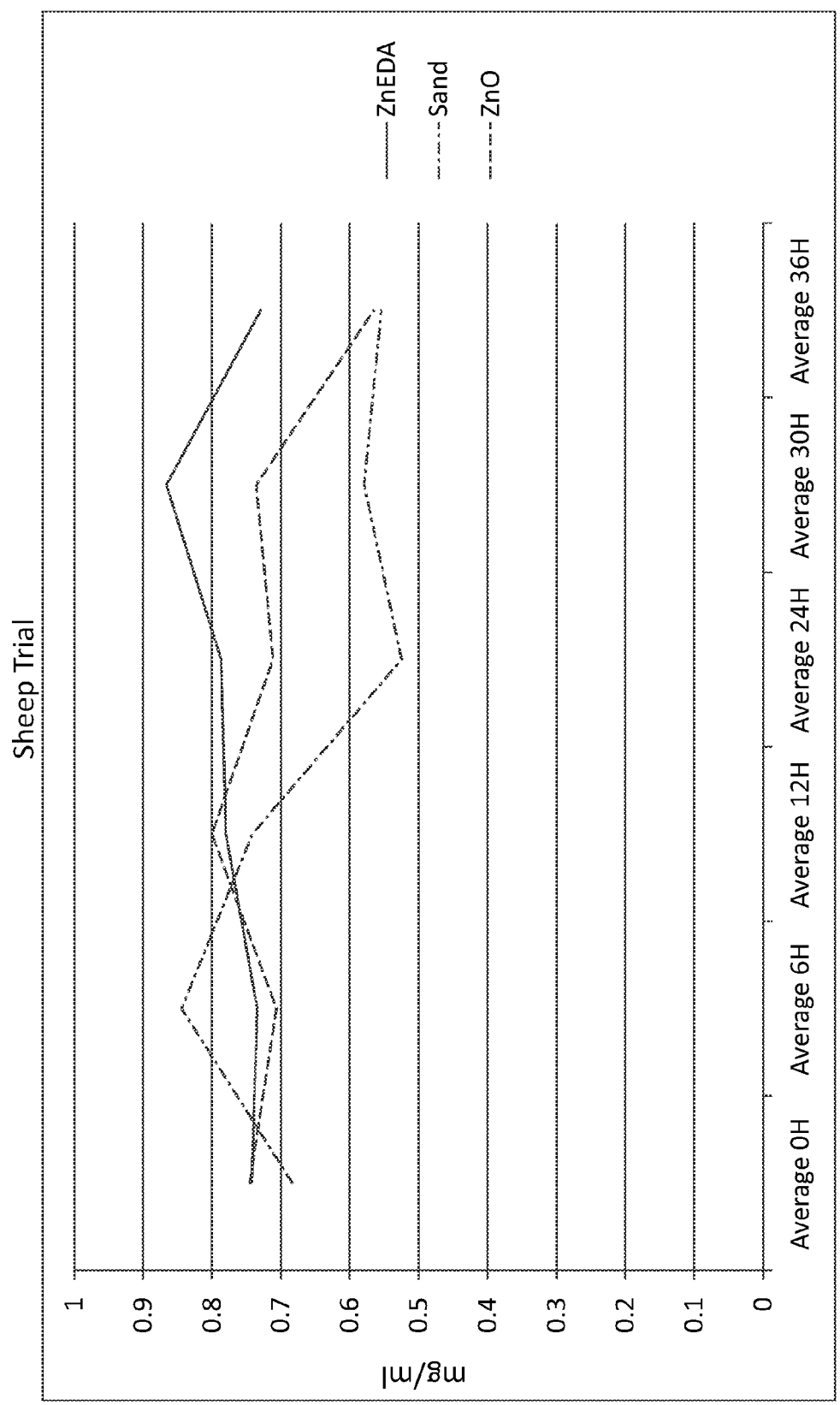
FIG. 2 shows a graph of comparative sheep results for Zn-EDA, and ZnO and sand.

Sheep were given a 250 mg bolus of zinc from ZnSO$_4$ at time 0. Then at 6 hours they were given another bolus of either no zinc (sand) zinc oxide or Zn-EDA. The serum zinc levels were the highest and higher for a longer duration with the Zn-EDA than the other treatments. The results are shown in FIG. 2.

Example 20

Poultry Trial

Animals were Cobb male broilers. The experiment was started with 1 day old animals. ZnSO$_4$ was used as a comparative example using 80 ppm zinc from ZnSO$_4$. Zn-EDA replaced 40 ppm of the zinc so there was 40 ppm Zn from ZnSO$_4$ and 40 ppm Zn from Zn-EDA and compared to 80 ppm Zn from ZnSO$_4$. Actual broiler integrator diets were used. They contain 500 ftu of phytase and an NSP enzyme (nonstarch polysaccride degrading enzyme). The plane of nutrition is targeted to be at AgriStat's 75$^{th}$ percentile. The experiment had a completely randomized design. There were 12 replicates per treatment and 21 birds per replicate.

The following Table 1 shows the data that is represented for the poultry trial with Cobb male broilers. It demonstrates in a statistically significant way the improved feed conversion and lower mortality when the invention is practiced.

TABLE 1

| Treatment | Body Wt., Kg | Feed Conversion | Mortality, % |
|---|---|---|---|
| ZnSulfate[a] | 2.212 | 1.531 | 4.71 |
| Zn-EDA[b,c] | 2.200 | 1.500 | 1.81 |
| P-value | 0.160 | 0.031 | 0.214 |

[a]Dietary supplemental zinc = 80 ppm
[b]Replaced 40 ppm Zn from Sulfate source
[c]Zn content for ZnEDA was 24.1

In the following examples sheep were given a bolus injection like in Example 19 and then blood uptake was measured at various intervals. For some reason the 30 hour level seems to be an observed best point for differentiation based upon past experiments with EDA.

Example 21

Figure 3:
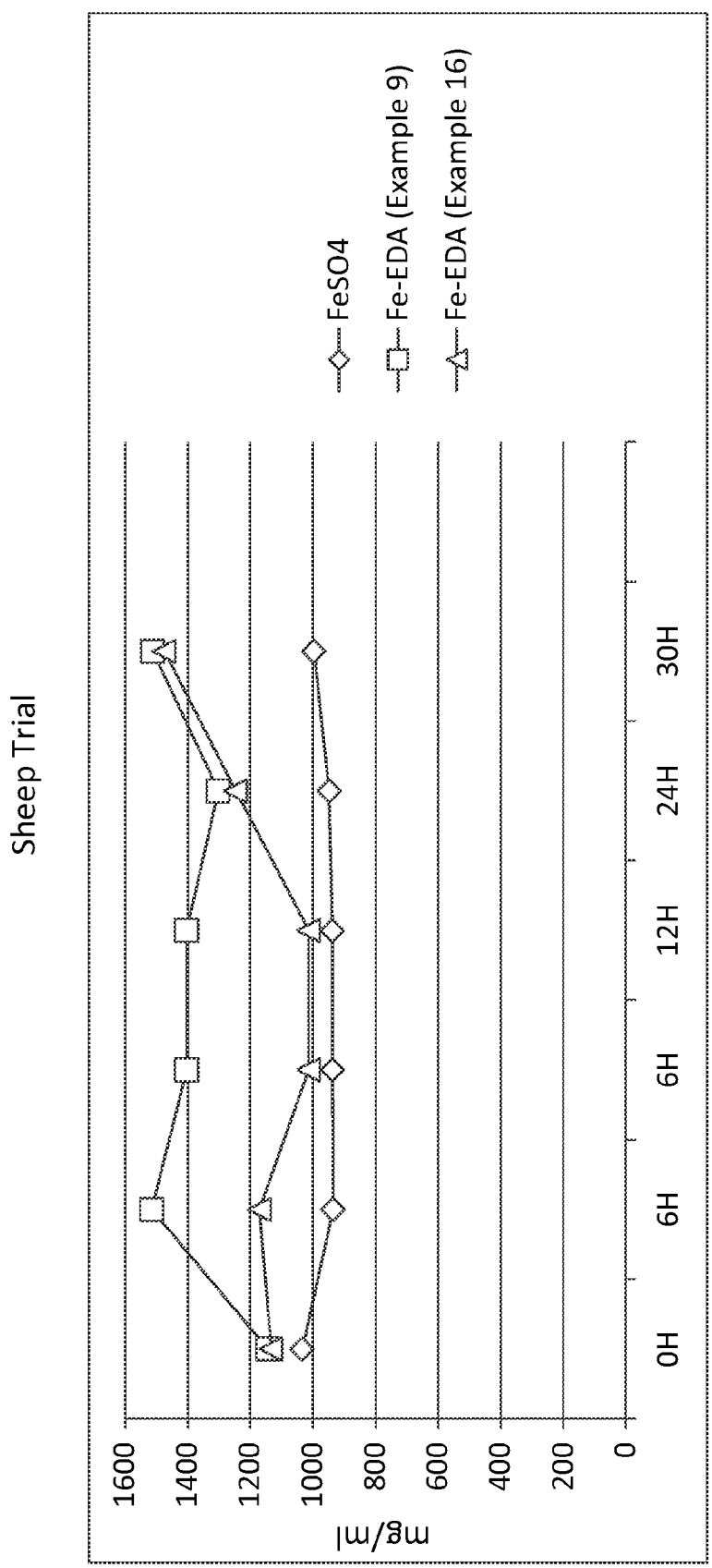
FIG. 3 shows a graph of comparative sheep data of Examples 9 and 16.

The Fe-EDA (Example 9) and the Fe-EDA (Example 16) were tested for iron uptake in the blood in comparison with the bolus injection of FeSO$_4$. As can be seen in FIG. 3 the Fe-EDA samples were better at every interval than inorganic iron sulfate, most notably at 30 hours.

Example 22

Tests like in Example 19 and 21 were run with MnSO$_4$ in comparison with Mn-EDA of Example 10. At all points Manganese blood uptake of the sheep was at lower levels than other tested ligands. This may be a characteristic of Mn itself. However the data at 30 hours did show a significant difference in comparison with inorganic MnSO$_4$.

| 30 hour | |
|---|---|
| MnSO$_4$ | 24 |
| Mn-EDA (Example 10) | 33 |

From the above, it can be seen that the invention does accomplish at least all of its stated objectives.

What is claimed is:

1. A method of nutritionally supplementing the diet of animals with trace minerals, comprising:

feeding an animal a small but trace mineral supplementing effective amount of an ethylene diamine (EDA) metal ligand of the formula:

M(EDA)X, wherein M is a metal selected from the group consisting of zinc, iron, copper and manganese, EDA is ethylene diamine ligated to the metal, and X represents counterions selected to provide a neutral metal and/or ligand.

2. The method of claim 1 wherein the animal is a domesticated livestock or poultry animal.

3. The method of claim 1 wherein prior to feeding, the metal ethylene diamine neutral ligand is mixed with a non-toxic carrier.

4. The method of claim 3 wherein the carrier is selected from the group consisting of sugars, fermentation solubles, feed grains, corn cob flour, cellulose, and whey.

5. The method of claim 4 wherein the diet supplementing amount of said metal ligand complex is sufficient to meet the animals daily needs of the metal selected.

* * * * *